United States Patent
Benje et al.

(10) Patent No.: US 11,820,722 B2
(45) Date of Patent: Nov. 21, 2023

(54) METHOD AND PLANT FOR PREPARING VINYL CHLORIDE FROM 1,2-DICHLOROETHANE

(71) Applicants: THYSSENKRUPP AG, Essen (DE); THYSSENKRUPP INDUSTRIAL SOLUTIONS AG, Essen (DE); VINNOLIT GMBH & CO. KG, Burgkirchen (DE)

(72) Inventors: Michael Benje, Bad Soden (DE); Peter Kammerhofer, Burgkirchen (DE); Klaus Krejci, Burghausen (DE)

(73) Assignees: Vinnolit GmbH & Co. KG, Burgkirchen (DE); Thyssenkrupp AG, Essen (DE); Thyssenkrupp Industrial Solutions AG, Essen (DE)

( * ) Notice: Subject to any disclaimer, the term of this patent is extended or adjusted under 35 U.S.C. 154(b) by 144 days.

(21) Appl. No.: 17/607,096

(22) PCT Filed: Apr. 22, 2020

(86) PCT No.: PCT/EP2020/061201
§ 371 (c)(1),
(2) Date: Oct. 28, 2021

(87) PCT Pub. No.: WO2020/221638
PCT Pub. Date: Nov. 5, 2020

(65) Prior Publication Data
US 2022/0227689 A1   Jul. 21, 2022

(30) Foreign Application Priority Data
Apr. 30, 2019   (DE) .................... 10 2019 206 155.9

(51) Int. Cl.
*C07C 17/25* (2006.01)
*B01J 19/00* (2006.01)

(52) U.S. Cl.
CPC ............ *C07C 17/25* (2013.01); *B01J 19/0013* (2013.01); *B01J 2219/00132* (2013.01); *B01J 2219/00157* (2013.01)

(58) Field of Classification Search
CPC ................................ C07C 17/25; C07C 21/06
See application file for complete search history.

(56) References Cited

U.S. PATENT DOCUMENTS

| 4,721,604 A | 1/1988 | Simonetta et al. |
| 4,798,914 A | 1/1989 | Link et al. |

(Continued)

FOREIGN PATENT DOCUMENTS

| DE | 1 010 800 B | 2/1966 |
| DE | 1 210 800 B | 2/1966 |

(Continued)

OTHER PUBLICATIONS

Intellectual Property India, First Examination Report in Indian Patent Application No. 202117049551 (dated Mar. 9, 2022).

(Continued)

*Primary Examiner* — Jafar F Parsa
(74) *Attorney, Agent, or Firm* — Leydig, Voit & Mayer, Ltd.

(57) ABSTRACT

The present invention relates to a method for preparing vinyl chloride by catalytic thermal cracking of 1,2-dichloroethane, in which method the heat required for the thermal cracking is supplied via a liquid or condensing heat transfer medium. The present invention also relates to a plant for preparing vinyl chloride by catalytic thermal cracking of 1,2-dichloroethane, in which the heat required for the thermal cracking, as well as for the preceding preheating, evaporation and optionally overheating of the 1,2-dichloroethane, is supplied via a liquid or condensing heat transfer medium, said plant comprising at least one reactor in which the thermal crack- (Continued)

ing takes place and at least one first heating device by means of which heat is transported to the reaction medium in the reactor by means of the liquid or condensing heat transfer medium.

16 Claims, 2 Drawing Sheets

(56) References Cited

U.S. PATENT DOCUMENTS

| | | | |
|---|---|---|---|
| 4,843,182 | A | 6/1989 | Simonetta et al. |
| 9,334,209 | B2 | 5/2016 | Braun |
| 9,481,620 | B2 | 11/2016 | Benje et al. |
| 9,951,979 | B2 | 4/2018 | Aga et al. |
| 2014/0336426 | A1 | 11/2014 | Benje et al. |
| 2015/0353452 | A1 | 12/2015 | Braun |
| 2016/0222830 | A1 | 8/2016 | Aga et al. |

FOREIGN PATENT DOCUMENTS

| | | |
|---|---|---|
| DE | 1 468 827 A1 | 12/1969 |
| DE | 102 52 891 A1 | 5/2004 |
| EP | 0 002 021 A1 | 5/1979 |
| EP | 0 264 065 A1 | 4/1988 |
| EP | 0 270 007 A2 | 6/1988 |
| GB | 1244216 A | 8/1971 |
| GB | 1527464 A | 10/1978 |
| JP | S48-7407 B | 3/1973 |
| JP | S52-111524 A | 9/1977 |
| JP | 2016-142272 A | 8/2016 |
| RU | 1773258 A3 | 10/1992 |
| WO | WO 2013/083230 A1 | 6/2013 |
| WO | WO 2014/108159 A1 | 7/2014 |

OTHER PUBLICATIONS

Indonesian Patent Office, First Examination Report in Indonesian Patent Application No. P00202109738 (dated Dec. 12, 2022).
Federal Institute of Industrial Property, Office Action in Russian Patent Application No. 2021131803/04 (067403) (dated Jun. 14, 2022).
European Patent Office, International Search Report in International Application No. PCT/EP2020/061201 (dated Jul. 16, 2020).
European Patent Office, Written Opinion in International Application No. PCT/EP2020/061201 (dated Jul. 16, 2020).
International Bureau of WIPO, International Preliminary Report on Patentability in International Application No. PCT/EP2020/061201 (dated Nov. 2, 2021).
Koning, "Molten Salt Systems other Applications link to Solar Power Plants," NREL Trough Meeting 2007, Pratteln, Switzerland (2007) 34 pgs.
Japan Patent Office, Notification of Reasons for Refusal in Japanese Patent Application No. 2021-564845 (dated Feb. 7, 2023).
U.S. Appl. No. 17/607,262, filed Oct. 25, 2021.

(Standby)

METHOD AND PLANT FOR PREPARING VINYL CHLORIDE FROM 1,2-DICHLOROETHANE

CROSS-REFERENCE TO RELATED APPLICATIONS

This patent application is the U.S. national phase of International Application No. PCT/EP2020/061201, filed on Apr. 22, 2020, which claims the benefit of German Patent Application No. 10 2019 206 155.9, filed Apr. 30, 2019, the disclosures of which are incorporated herein by reference in their entireties for all purposes.

The present invention relates to a method for producing vinyl chloride by catalytic thermal cleavage of 1,2-dichloroethane, in which the heat required for the thermal cleavage is supplied via a liquid or condensing heat transfer medium. The subject matter of the present invention is further a plant for producing vinyl chloride by catalytic thermal cleavage of 1,2-dichloroethane, in which the heat required for thermal cleavage as well as for the precursory preheating, evaporating and optionally overheating the 1,2-dichloroethane is supplied via a liquid or condensing heat transfer medium, comprising at least one reactor in which the thermal cleavage takes place and at least one first heating device, by means of which a heat transfer to the reaction medium in the reactor takes place by means of the liquid or condensing heat transfer medium.

The thermal cleavage of 1,2-dichloroethane for producing vinyl chloride, which is required particularly for producing polyvinyl chloride, follows the reaction equation (1) shown below:

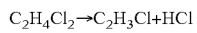

It is an endothermic reaction wherein the pyrolysis can be carried out either without a catalyst in the gas phase under high pressure of 1 to 3 MPa and at a temperature of 450 to 600° C. or also in catalytic methods that allow the pyrolysis to occur lower temperatures. In catalytic methods, too, the reaction is predominantly carried out in the gas phase.

PRIOR ART

For example, a method for producing vinyl chloride by thermal cleavage of 1,2-dichloroethane is described in EP 264 065 A1, in which 1,2-dichloroethane is heated in a first container, then transferred to a second container in which it is evaporated without further heating under lower pressure than in the first container and the gaseous 1,2-dichloroethane is fed into a cracking furnace, in which the cleavage to vinyl chloride and hydrogen chloride takes place. The temperature of the 1,2-dichloroethane is 220° C. to 280° C. when it leaves the second container. In the cracking furnace, pipes in which the 1,2-dichloroethane is thermally cleaved are heated by means of a fossil fuel. The gaseous 1,2-dichloroethane is heated to 525° C. or 533° C. in the radiation zone of the cracking furnace.

EP 264 065 A1 also mentions that a temperature control medium can be used to preheat the liquid, fresh 1,2-dichloroethane, which temperature control medium in turn is heated in the convection zone of the cracking furnace with the flue gas produced by the burners heating the cracking furnace. Heated, high-boiling liquids such as mineral oil, silicone oil or molten diphenyl are suitable as the temperature control medium. However, only preheating to a temperature of 150 to 220° C. takes place in this way, while the pyrolysis takes place even at temperatures of around 530° C. In this known method, there is therefore no provision for the pyrolysis to be carried out at temperatures in the range from 300 to 400° C. and for all the necessary supply of heat to be carried out with the aid of a liquid or vaporous heat transfer medium.

As a rule, a plant complex for producing vinyl chloride consists of
- a plant for producing 1,2-dichloroethane from ethene and chlorine ("direct chlorination"),
- a plant for producing 1,2-dichloroethane from ethene, hydrogen chloride and oxygen ("oxychlorination"),
- a plant for the purification of 1,2-dichloroethane by distillation,
- a plant for the thermal cleavage of the 1,2-dichloroethane purified by distillation to vinyl chloride and hydrogen chloride and
- a plant for the distillative separation of the hydrogen chloride and unconverted 1,2-dichloroethane and for the purification of the vinyl chloride.

The hydrogen chloride obtained by thermal cleavage of the 1,2-dichloroethane can be returned to the oxychlorination plant, where it can be reacted again with ethene and oxygen to form 1,2-dichloroethane.

In the method described in DE 102 52 891 A1 for the cleavage of 1,2-dichloroethane into vinyl chloride and hydrogen chloride, a catalyst is used which allows the operating temperature to be reduced during the endothermic cleavage. However, in this method too, the tubular reactor is fired with a primary energy source such as oil or gas, wherein the furnace is divided into a radiation zone and a convection zone. In the radiation zone, the heat required for pyrolysis is mainly transferred to the reaction tube by radiation from the furnace walls, which are heated by the burner. In the convection zone, the energy content of the hot flue gases emerging from the radiation zone is used by convective heat transfer, whereby the 1,2-dichloroethane as the starting material of the pyrolysis reaction can be preheated, evaporated or overheated.

Various measures for saving energy and/or heat recovery in plants for producing 1,2-dichloroethane are known from the prior art. Such measures lead to a significant reduction in operating costs and thus make a significant contribution to the profitability of the plant and to a reduction in the $CO_2$ emissions of the plant. These are, for example, measures that use the heat of reaction from the exothermic reaction steps to heat heat sinks in the process. WO 2014/108159 A1 lists various known measures for heat recovery in plants for producing vinyl chloride and names the corresponding literature references.

EP 0 002 021 A1 describes a method for the catalytic dehydrohalogenation of 1,2-dichloroethane to vinyl chloride in which zeolitic catalysts which have been treated with a Lewis acid are used. When using such catalysts, it is possible to carry out the reaction at elevated pressure and temperatures in the range from 200° C. to 400° C. and thus considerably lower temperatures than in the conventional pyrolysis of 1,2-dichloroethane.

The object of the present invention is to provide an improved method for producing vinyl chloride by thermal cleavage of 1,2-dichloroethane, in which a reduction in operating costs, a significant reduction in $CO_2$ emissions and the provision of electrical control power is achieved.

The solution to the aforementioned problem is provided by a method for producing vinyl chloride by catalytic thermal cleavage of 1,2-dichloroethane of the type mentioned above and as described herein.

A method for purely thermal (uncatalyzed in a pyrolysis furnace) or thermal-catalytic EDC cleavage (with the supply of heat when using a catalyst) usually consists of the sub-steps:

preheating of liquid 1,2-dichloroethane up to the evaporation temperature at the given pressure evaporating the preheated 1,2-dichloroethane if necessary, overheating of the vaporous 1,2-dichloroethane up to the range of the reaction temperature (if the previous evaporation did not take place in the range of the reaction temperature)

cleavage reaction (purely thermal or thermal using a catalyst) with the supply of heat.

The subject matter of the invention is a method which, in addition to heating the catalytic-thermal cleavage reaction by a liquid or condensing heat transfer medium, also enables the upstream preheating, evaporation or overheating of the 1,2-dichloroethane to be heated by this heat transfer medium. Not all of these steps have to be heated by means of the heat transfer medium. The method according to the invention comprises the heating of at least one up to any combination of the above-mentioned sub-steps, wherein it is possible for the individual sub-steps in turn to be subdivided (in terms of apparatus) into individual steps.

DETAILED DESCRIPTION OF THE INVENTION

Figure 1:
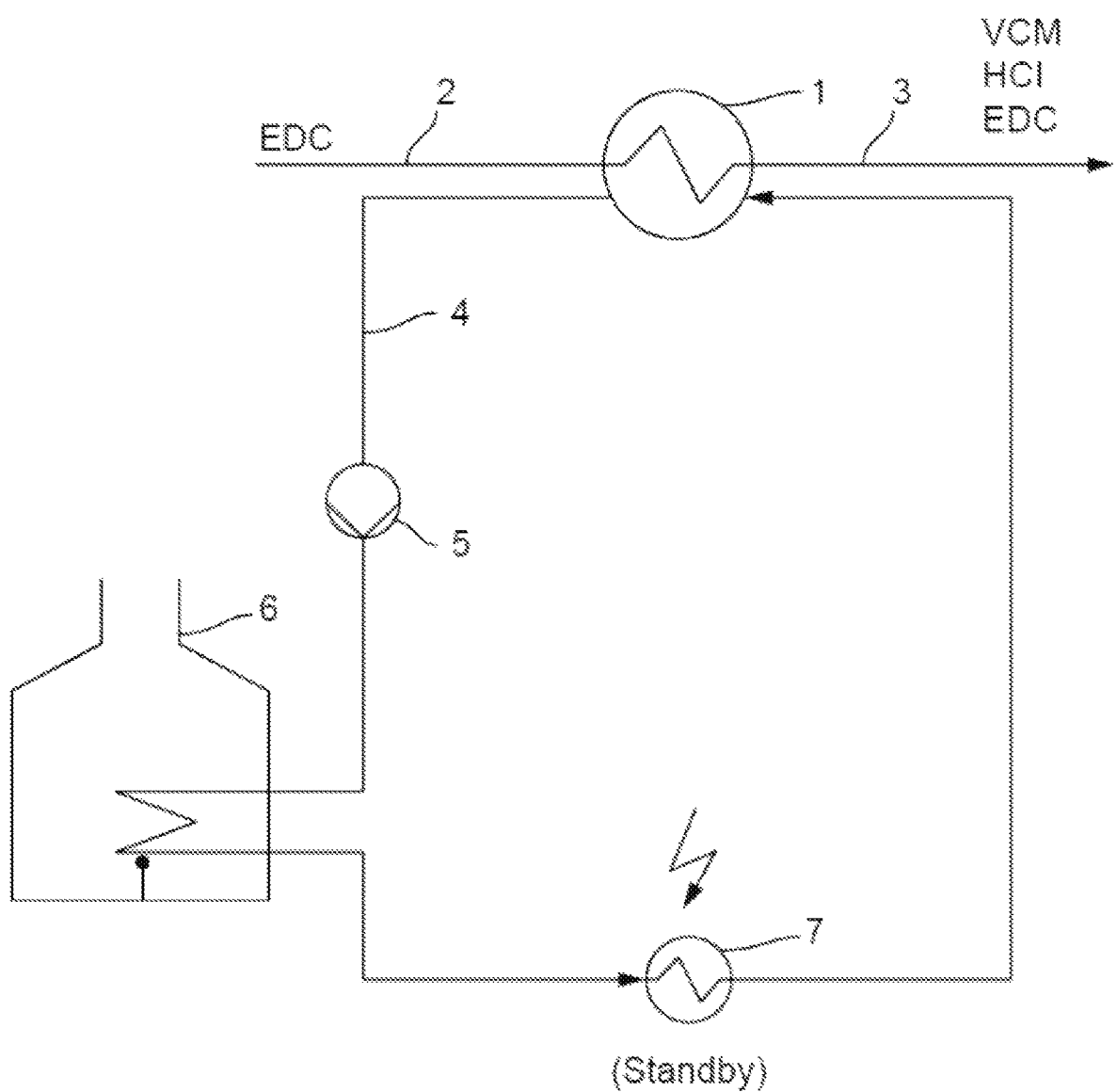
FIG. 1 depicts an embodiment of a plant for producing vinyl chloride by catalytic thermal cleavage of 1,2-dichloroethane, in which the heat required for thermal cleavage is supplied via a liquid or condensing heat transfer medium. Part (1) represents a reactor in which the thermal cleavage takes place. Part (6) represents a first heating device by which heat is a supplied to the reaction medium in the reactor takes place. Part (4) represented a heat transfer medium. Part (5) represents a pump integrated into a line system. Part (7) represents a second heating device for heating the heat transfer medium.
Figure 2:
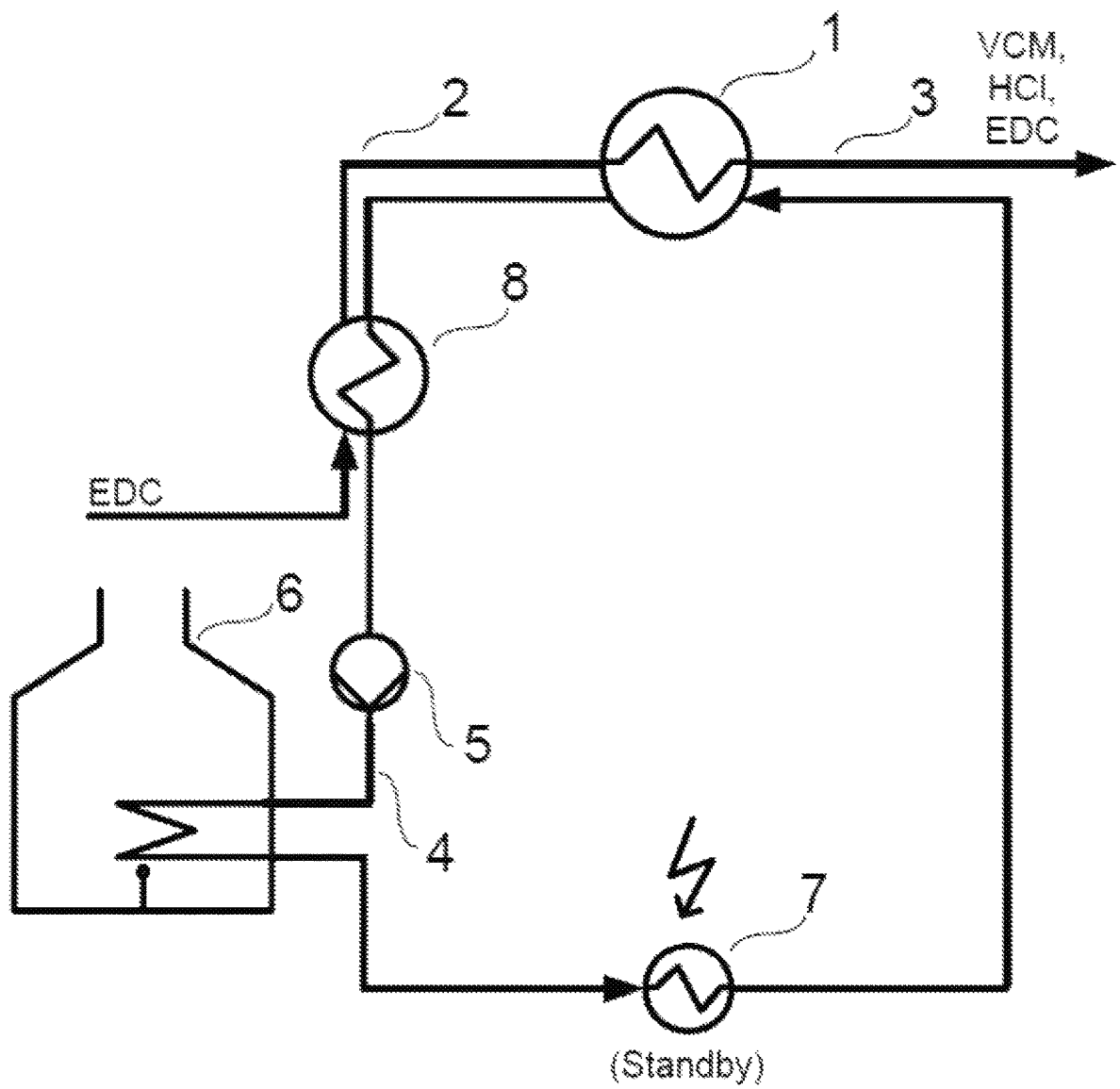
FIG. 2 depicts another embodiment of a plant for producing vinyl chloride by catalytic thermal cleavage of 1,2-dichloroethane, in which the heat required for thermal cleavage is supplied via a liquid or condensing heat transfer medium. Here, at least one device (8) for heating and/or evaporating and/or overheating the starting material 1,2-dichloroethane is integrated into the circuit of the heat transfer medium (4).

"Heating" in the context of the method according to the invention means the transfer of heat to the starting material 1,2-dichloroethane and/or the reaction mixture by means of a heat transfer medium. The starting material 1,2-dichloroethane can be heated, evaporated or overheated. The reaction mixture in the reactor can be supplied with heat at a constant temperature level (isothermal reaction procedure). The reaction mixture can also heat up further, wherein the heat supplied by the heating is used partly to cover the heat requirement for the reaction and partly to further heat the reaction mixture. Finally, the heat supply to the reaction mixture can be adjusted by heating so that the sensible heat content of the reaction mixture is at least partially used to cover the reaction heat requirement and the reaction mixture cools down in the reactor compared to the reactor inlet temperature. The heating and also the transfer of heat to the starting material 1,2-dichloroethane is carried out by a liquid heat transfer medium while cooling the heat transfer medium or reducing its sensible heat content and/or by a condensing heat transfer medium that was previously evaporated by means of a heating device.

Heating by a liquid heat transfer medium while cooling the heat transfer medium or reducing its sensible heat content is particularly preferable. However, the method according to the invention also comprises the transfer of heat to the starting material 1,2-dichloroethane and/or by condensing heat transfer medium that was previously evaporated by means of a heating device, utilizing the latent heat content of the heat transfer medium.

Heating devices for the heat transfer medium in the context of the method according to the invention are, on the one hand, devices (heaters and/or evaporators or devices in which a heater and an evaporator function are combined) that can be heated by means of a fossil fuel such as heating oil or preferably natural gas. On the other hand, these are electrical heat transfer devices (heaters and/or evaporators or devices in which a heater and an evaporator function are combined). Such devices are known to those skilled in the art.

The heating devices, in turn, may consist of several sub-units, for example, may be several ovens connected in parallel or several electrical heaters connected in parallel for heating thermal oil.

Adjustment of the heat output of the heating devices can be accomplished both by varying the heat output of one or more sub-units, or by turning one or more sub-units on and off, or by any combination of these measures.

Heating devices for the 1,2-dichloroethane or the reaction mixture can be any type of heat exchanger known to those skilled in the art, for example, but not limited to: Tube bundle heat exchangers, plate heat exchangers, double tube heat exchangers, spiral heat exchangers, natural circulation evaporators or forced circulation evaporators.

Heat transfer media in the sense of the method according to the invention can be, for example, mineral and synthetic thermal oils, silicone oils as well as molten salts.

According to the invention, the liquid (or condensing, see above) heat transfer medium is at least temporarily and/or at least partially or completely electrically heated. This creates the possibility of at least temporarily making available the heat required for the thermal cleavage from inexpensive electrical energy. For example, during periods when inexpensive excess electrical energy is available, preferably from renewable sources, such as at night or during periods of high wind or solar radiation, the heat required for the reaction can be quickly provided by electrical energy. This has the advantage of reducing the plant's operating costs and lowering $CO_2$ emissions, which benefits climate protection. Likewise, electrical balancing power or load can be made available to the energy supplier in this way.

According to a preferred further development of the method according to the invention, the heat required for the reaction is at least temporarily exclusively provided by electrically heating the heat transfer medium. This preferred variant of the method provides that the heat required for the reaction is generally made available via a first heating device which can be heated by means of fossil fuels, for example, but an electrically operated second heating device that can be used temporarily, for example when inexpensive electricity from renewable resources sources is available, is present. In these cases, the first heating device can be throttled or, possible, shut down completely for a certain period of time, or also the heat transfer medium can be guided such that it partially or completely bypasses the first heating device in terms of flow.

According to a preferred further development of the method according to the invention, the liquid heat transfer medium is heated at least temporarily and/or at least partly by the combustion of at least one fuel and partly by electrically heating. The use of a liquid or condensing heat transfer medium to provide all of the heat of reaction that is required for the pyrolytic cleavage of 1,2-dichloroethane is made possible by carrying out the reaction in the presence of suitable catalysts, which enable the reaction temperature to be reduced significantly compared to conventional methods without catalysis. When using such catalysts, the reaction can be reduced, for example, from the temperatures customary in conventional methods in the order of magnitude of about 450° C. to about 530° C. to temperatures in the range of particularly about 200° C. to 400° C. Heating to temperatures by means of the sensible heat content of a liquid heat transfer medium in this range or heat transfer by condensation of, for example, a heat transfer oil in this range is possible, for example, when using a heat transfer oil or possibly (only in the liquid phase) a molten salt. Substances such as those mentioned in the above-mentioned EP 0 002 021 A1 can be considered as a catalyst.

According to a preferred further development of the method according to the invention, at least one first heating device operated by combustion of at least one fuel and additionally at least one electrically operated second heating device are used for heating the liquid heat transfer medium and/or for evaporating the liquid heat transfer medium. If inexpensive electrical energy is not available, the required thermal energy for pyrolysis can then be provided by a first heating device that heats the heat transfer medium by burning a fuel such as methane or natural gas. This results in three alternative process variants, which make the method according to the invention very flexible. Either heating and/or evaporation is carried out only by means of the first heating device, or heating and/or evaporation is carried out, at least temporarily, only by means of the second electrical heating device, or both heating devices are used simultaneously for heating and/or evaporation of the reaction medium.

According to a preferred further development of the method according to the invention, the liquid heat transfer medium is conducted in a circuit and the at least one first heating device and the at least one electrically operated second heating device are integrated into this circuit.

According to a preferred further development of the method according to the invention, at least one first heating device and at least one electrically operated second heating device are connected in series in the circuit. The heat transfer medium then flows in a line circuit first through the first heating device and then downstream of this the second electrical heating device or, however, these two heating devices are flowed through in reverse order. As an alternative to this, it is also possible to arrange the two heating devices in parallel, as it were, that is, the line circuit in which the heating devices are integrated is connected and the corresponding lines can be shut off, for example, via valves, so that the heat transfer medium can flow through the second heating device without said heat transfer medium also flowing through the first heating device and possibly vice versa.

According to a preferred further development of the method according to the invention, the heat transfer medium is conveyed in a circuit in which a reactor is integrated, in which the catalytic thermal cleavage of 1,2-dichloroethane is carried out, wherein there is a heat exchange between the reaction medium of the reactor and the heat transfer medium.

According to a preferred further development of the method according to the invention, the heat transfer medium is conveyed in a circuit in which, in addition to the reactor, devices are also provided for preheating, evaporating and overheating the 1,2-dichloroethane before it enters the reactor.

According to a preferred further development of the method according to the invention, the heat transfer medium is conveyed in the circuit in countercurrent to the flow of the reaction medium through the reactor or through devices for preheating and/or for evaporating and/or for overheating the reaction medium. This variant is advantageous for effective heat transfer. As an alternative to this, however, a flow of the heat transfer medium in co-current with the flow of the reaction medium is also possible.

According to a preferred further development of the method according to the invention, the electrically operated second heating device is operated at least temporarily by means of electrical energy obtained from renewable sources. During periods when inexpensive excess electrical energy is available, preferably from renewable sources, such as at night or during periods of high wind or solar radiation, or when the energy supplier demands a control load, the heat required for the reaction can be quickly provided by electrical energy.

According to a preferred further development of the method according to the invention, the electrically operated second heating device is operated in standby mode. In this variant of the method, it is provided that the electrically operated second heating device is preferably permanently at operating temperature. For example, a small volume of the liquid heat transfer medium can always flow through this second electrical heating device, or a small amount of the heat transfer medium can always be evaporated and condensed again. This has the advantage that, in the event of a demand for heat from the second heating device, the heat transfer medium can be made available in liquid or vapor form at the desired temperature in a short time without requiring a lengthy heating phase to the operating temperature of the heating device. For this purpose, the system can have a controller, for example, which then starts up the respective heating device in the event of a demand and requests the higher electrical power required for this purpose. Instead of a system with a control system, however, it is also possible in principle to carry out a start-up of the second heating device and a shut-down of the first heating device via an operator.

According to a preferred further development of the method according to the invention, the thermal cleavage of 1,2-dichloroethane is carried out in a temperature range from 200° C. to 400° C. This is a preferred temperature range which can be easily implemented using liquid or vaporous heat transfer media, for example, heat transfer oils.

The subject matter of the present invention is further a plant for producing vinyl chloride by catalytic thermal cleavage of 1,2-dichloroethane, in which the heat required for preheating, evaporation and overheating and for the thermal cleavage of 1,2-dichloroethane is supplied via a liquid or condensing heat transfer medium, comprising at least one reactor in which the thermal cleavage takes place and at least one first heating device by means of which a heat transfer to the reaction medium in the reactor takes place by means of the liquid or condensing heat transfer medium, wherein the plant according to the invention also comprises at least one second electrical heating device for heating the reaction medium. Compared to conventional plants, the plant according to the invention has the advantage that the thermal energy required for the thermal cleavage of the 1,2-dichloroethane can optionally be provided only by the second heating device or only by the first heating device or also cumulatively by both heating devices.

A preferred development of the invention provides that the reactor is integrated into a circuit of the heat transfer medium, wherein at least the electrically operated second heating device is also integrated into the circuit.

A further preferred further development of the invention is that, in addition to the reactor, devices for preheating, evaporating and overheating of the starting material 1,2-dichloroethane are also incorporated in a circuit of the heat transfer medium.

According to a preferred variant of the invention, at least one first heating device operated via fuel and furthermore at least one electrically operated second heating device are integrated into the circuit of the heat transfer medium.

According to a preferred variant of the invention, the circuit of the heat transfer medium comprises a pump integrated into a line system, at least one first heating device operated via a fuel, at least one electrically operated second heating device and the reactor, wherein means for transferring heat from the heat transfer medium to devices for preheating, evaporating and overheating as well as a reaction medium flowing through the reactor or located in the reactor are provided.

A preferred further development of the invention provides that the first heating device operated via fuel and the electrically operated second heating device are arranged in series or, alternatively, in parallel in the circuit of the heat transfer medium.

The invention claimed is:

1. A method for producing vinyl chloride by thermal cleavage of 1,2-dichloroethane, in which heat required for thermal cleavage is supplied via a liquid or condensing heat transfer medium, wherein the heat transfer medium is at least temporarily electrically heated, wherein at least one first heating device operated by combustion of at least one fuel and additionally at least one second heating device operated electrically are utilized to heat the liquid heat transfer medium, wherein the heat transfer medium is a mineral oil, a synthetic thermal oil, a silicon oil, or a molten salt, and the thermal cleavage of the 1,2-dichloroethane is carried out as a catalytic thermal cleavage in a temperature range from 200° C. to 400° C.

2. The method according to claim 1, wherein the heat required for the thermal cleavage is temporarily exclusively provided by electrically heating the heat transfer medium.

3. The method according to claim 1, wherein the 1,2-dichloroethane is preheated and/or evaporated and/or overheated by means of the heat transfer medium.

4. The method according to claim 1, wherein the heat transfer medium is heated at least temporarily by the combustion of at least one fuel and partially by electrical heating.

5. The method according to claim 1, wherein the heat transfer medium is conducted in a circuit and the at least one first heating device and the at least one second heating device operated electrically are integrated into this circuit.

6. The method according to claim 1, wherein at least one first heating device and at least one second heating device operated electrically are connected in series or in parallel in a circuit.

7. The method according to claim 1, wherein the heat transfer medium is conducted in a circuit into which a reactor is integrated, in which the catalytic thermal cleavage of 1,2-dichloroethane is carried out, wherein a heat exchange takes place between the reaction medium of the reactor and the heat transfer medium.

8. The method according to claim 1, wherein the heat transfer medium is conducted in a circuit in which devices for preheating and/or evaporating and/or overheating are integrated in addition to the reactor in which the catalytic thermal cleavage of 1,2-dichloroethane is carried out, wherein a heat exchange takes place between the reaction medium and the heat transfer medium.

9. The method according to claim 8, wherein the heat transfer medium is conducted in the circuit in countercurrent to the flow of the reaction medium through the reactor.

10. The method according to claim 1, wherein the second heating device operated electrically is operated at least temporarily by electrical energy obtained from renewable sources.

11. The method according to claim 1, wherein the second heating device operated electrically is operated in standby mode.

12. A plant for producing vinyl chloride by thermal cleavage of 1,2-dichloroethane, in which heat required for thermal cleavage is supplied via a liquid or condensing heat transfer medium, comprising at least one reactor in which catalytic thermal cleavage of 1,2-dichloroethane takes place and at least one first heating device by which a supply of heat to the reaction medium in the reactor takes place by the liquid or condensing heat transfer medium, wherein the system further comprises at least one electrical second heating device for heating the heat transfer medium, wherein the heat transfer medium is a mineral oil, a synthetic thermal oil, a silicon oil, or a molten salt, and the heating devices are configured to heat the heat transfer medium for the catalytic thermal cleavage of the 1,2-dichloroethane to be carried out in a temperature range from 200° C. to 400° C.

13. The plant according to claim 12, wherein the reactor is integrated into a circuit of the heat transfer medium, wherein additionally at least the second electrical heating device is integrated into the circuit.

14. The plant according to claim 12, wherein at least one first heating device operated via a fuel and further at least one second electrical heating device as well as at least one device for heating and/or evaporating and/or overheating the starting material 1,2-dichloroethane is integrated into the circuit of the heat transfer medium.

15. The plant according to claim 12, wherein the circuit of the heat transfer medium comprises a pump integrated into a line system, at least one first heating device operated via a fuel, at least one second electrical heating device and the reactor, wherein means for transferring heat from the heat transfer medium to a reaction medium flowing through the reactor are provided.

16. The plant according to claim 14, wherein the first heating device operated via a fuel and the electrical second heating device are arranged in series or in parallel in the circuit of the heat transfer medium.

* * * * *